United States Patent [19]
Bozano

[11] Patent Number: 4,889,115
[45] Date of Patent: Dec. 26, 1989

[54] AIR REGULATOR FOR BREATHING APPARATUS

[76] Inventor: Enrico D. Bozano, 4/f, Via N. Oderico, 16145 Genova, Italy

[21] Appl. No.: 117,830

[22] Filed: Nov. 9, 1987

[30] Foreign Application Priority Data

Nov. 12, 1986 [IT] Italy ................................ 12570 A/86

[51] Int. Cl.⁴ ................................................ A61M 16/00

[52] U.S. Cl. ........................... 128/204.26; 128/204.29; 128/205.24

[58] Field of Search .......... 128/204.29, 204.26–205.24

[56] References Cited

U.S. PATENT DOCUMENTS

| | | | |
|---|---|---|---|
| 2,887,104 | 5/1959 | Sovinsky et al. | 128/203.11 |
| 3,783,891 | 1/1974 | Christianson | 128/204.26 |
| 4,219,017 | 8/1980 | Shamlian et al. | 128/204.26 |
| 4,694,825 | 9/1987 | Slemmer et al. | 128/205.24 |

*Primary Examiner*—Max Hindenburg
*Assistant Examiner*—J. P. Lacyk
*Attorney, Agent, or Firm*—Larson and Taylor

[57] ABSTRACT

The second stage of the regulator comprises a first airflow circuit, controlled by a manostat diaphragm in a conventional manner which permits the assumption of the minimum required amount of air upon each act of breathing, with a minimum effort; and a second airflow circuit combined with said first circuit, which permits to supply—in case of increased demand of air—a supplementary amount of air to meet any additional need of the user.

5 Claims, 1 Drawing Sheet

AIR REGULATOR FOR BREATHING APPARATUS

SUMMARY OF THE INVENTION

This invention relates to an air regulator for breathing apparatus, particularly for underwater breathing apparatus.

One of the most serious problems in the field of underwater breathing apparatus is to regulate the air flow rate supplied to a scuba-diver under particular conditions of oxygen requirements, such as when the scuba-diver is panting.

It is known that conventional regulators comprise a first stage for reducing the pressure of the air from the bottles, communicating with a second-stage reducing device which feeds the air into a hose to a mouthpiece for the user, the regulation of the amount of air supplied by said second-stage device upon each breathing act of the user being effected by valve-controlled devices under the action of a manostat diaphragm. These conventional devices supply, upon each breathing act, an amount of air which is independent of the actual need of a user, said amount being limited by the diameter of the holes through which the air is passed.

The main object of this invention, therefore, is to provide a regulator of the type mentioned above, wherein the second stage comprises a first airflow circuit, controlled by a manostat diaphragm in a conventional manner, which permits the assumption of the minimum required amount of air upon each act of breathing; and a second airflow circuit combined with said first circuit and in parallel therewith, which permits to supply—in case of deep or panting breathing of the user—a supplementary amount of air to meet any requirement of the user.

BRIEF DESCRIPTION OF THE DRAWING

Further characteristics and advantages of this invention will become apparent from the following detailed description of some preferred embodiments thereof, made with reference to the accompanying drawing which shows, by way of non-limiting examples, some preferred embodiments of the device according to the invention, and wherein.

DESCRIPTION OF THE PREFERRED EMBODIMENTS

Figure 1:
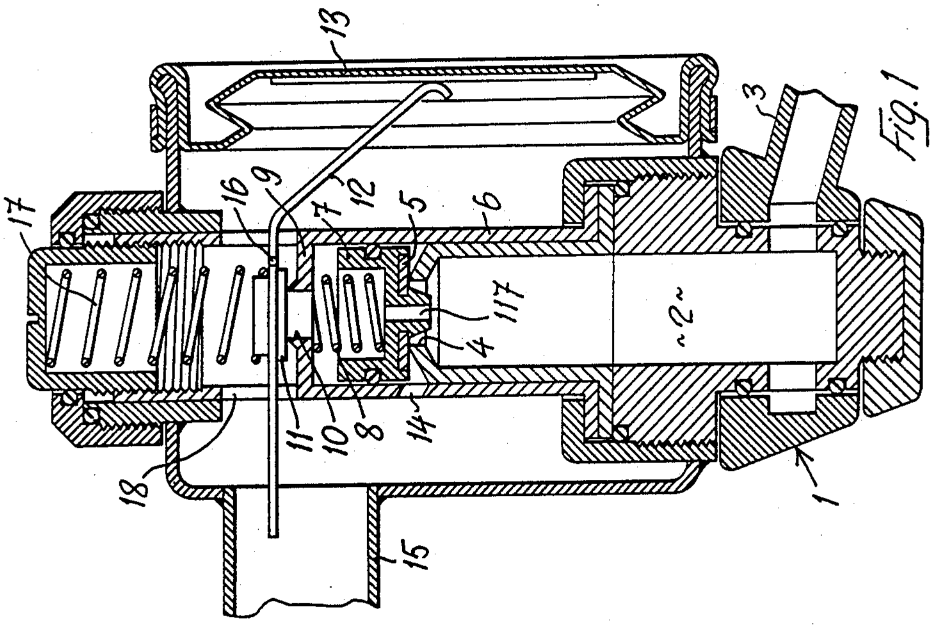
FIG. 1 is a diagrammatic, longitudinal sectional view of the second-stage device of a regulator according to the invention.

With reference to the drawing, and particularly to the FIG. 1 thereof, the illustrated device comprises, as known per se, a body member i formed with an interior cylindrical chamber 2 communicating at an end thereof with an air inlet conduit S connected to the first stage of the regulator, and including at the other end thereof an opening 4 which constitutes a valve seat on the outer side thereof. Concentric with the chamber 2 is a cylindrical conduit slidably accommodating a small piston 7. Said piston 7 is formed with an axial exactly-dimensioned hole 117 and comprises, on the end facing towards the valve seat 4 of said chamber 2, an annular seal 5 which normally rests against said valve seat to close it. Said piston 7 is constantly urged against the valve seat 4 by a spring B abutting at an end thereof against said piston 7 and at the other end thereof against an apertured partition 9 arranged across the conduit 0. Said partition 9 is provided with a central hole 10 which is formed as a valve seat on its side far from said piston 7. The valve seat on the hole 10 co-operates with a valve member 11 mounted on a pivotable lever 12 which co-operates with a manostat diaphragm 13 mounted on the body member 1 of the regulator. Said conduit B, upstream of the piston 7, is formed with a hole 14 for communicating with a conduit 15 which is connected to the mouthpiece for the user.

Said lever 12 is pivotably mounted on a fulcrum 10 and is constantly urged by a spring 17 housed within the body member 1, so as to seat the valve member 11 against the valve seat 10.

The operation of the device is now apparent.

In the position shown in FIG. 1, i.e. with the valve member 11 matched against the valve seat 10, and with the valve member 5 matched against the valve seat 4, the regulator prevents any flow of air from the conduit S to the conduit 15.

As soon as a user effects a breathing act (normal breathing condition), the reduced pressure created within the body member i causes, through the displacement of the diaphragm IS, the lever 12 to pivot against the action of the spring 17, whereby the valve member 11 is moved away from its valve seat permitting the air to flow from the conduit S to the chamber 2 and successively through the hole 4, the hole 117 of the piston 7, the valve seat 10 and the hole 18 in the wall of the conduit 6, downstream of the piston 7, to the conduit 15.

Whenever a larger amount of oxygen is required, for example, due to a panting condition, a still more reduced pressure is created and causes the piston 7 to be lifted from the seat 4 against the action of the spring B. In this instance, the air from the chamber 2 flows directly into the conduit 15 through the openings 4 and 14. A double flow of air to the conduit 15 is thus established to meet the user's increased demand of oxygen. As soon as this increased demand ceases, the valve member 5 of said piston 7 is urged back against its seat 4 to close it, whereby the supply of air will be regulated again by the valve member under the control of the diaphragm 13.

Figure 4:
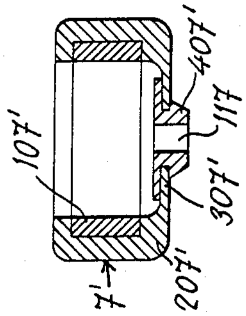
Figure 2:
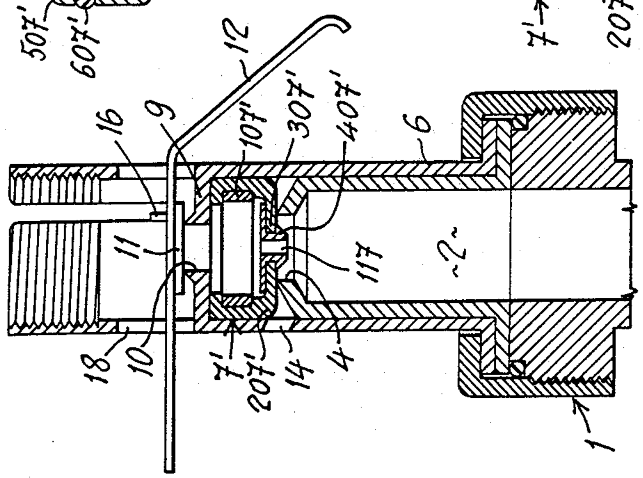

In the embodiment shown in the FIGS. 2 and 4, the piston 7 is replaced by a valve member 7′ comprising a metallic tubular element 107′ enwrapped circumferentially by a rubber shell 207′ extending radially inwards at one end thereof so as to form a diaphragm 307′ having a central hole wherein a metal nozzle 407′ with a central exactly-dimensioned through-hole 117 is sealingly embedded. According to this embodiment, the valve member 7′ is not slidable in the tubular conduit 6 as its upper end abuts against the partition 9 and its opposite end rests against the valve seat 4 through said diaphragm 307′. The operation of the just-described device is apparent. In the condition of increased air demand, the diaphragm 307′ is lifted from said seat 4 by virtue of its resiliency, thus permitting the air to pass from the seat 4 through the by-pass hole 14 to the conduit 15.

Figure 3:
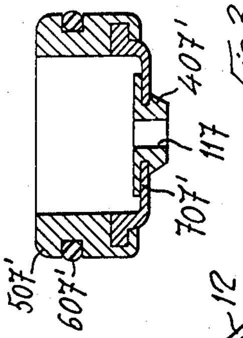
FIGS. 2 to 4 show some modifications of the valve member for the device according to the invention.

FIG. 3 shows a modification of the valve member 7′ of the FIGS. 2 and 4.

According to this modification, the valve member comprises a cylindrical metallic body 507′ provided with a sealing O-ring 007′ on its outer surface. The bottom end of the body 507′ is closed by a rubber diaphragm 707′ having a central hole wherein a nozzle 407′ with an exactly-dimensioned through-hole 117 is embedded.

The arrangement and operation of this valve member are exactly the same as those described above in connection with the embodiment of the FIGS. 2 and 4.

The advantages of the device of the invention are apparent.

During the normal use, the lever 12 is subjected to a minimum pressure and opens the valve member 11, thus permitting the flow of air through the exactly-dimensioned hole 117 and the opening 10 to the conduit 15 so as to permit a good breathing. If, due to any reason, the demand of air increases, the servo-control mechanism is activated whereby the larger valve 4 is opened and an additional flow of air is delivered to the conduit 15, through said by-pass circuit, so as to eliminate any damping condition immediately.

I claim:

1. An air regulator for a two-stage pressure reduction breathing apparatus for passing air from an inlet to a user's mouthpiece, wherein the second stage comprises:

first means defining a first airflow circuit to the user's mouthpiece of a size to permit a minimum required amount of breathing air to flow therethrough for allowing normal breathing by the user, a manostat diaphragm means operatively connected to the first means for permitting said minimum required amount of air to flow through the first airflow circuit upon each act of breathing by the user with a minimum of effort exerted by the user, second means defining a second airflow circuit to the user's mouthpiece, said second airflow circuit being in parallel with the first airflow circuit, and means operatively connected to the second means to open the second airflow circuit in response to forced damping or inhalation by the user, to supply directly to the user's mouthpiece a supplementary amount of breathing air to meet any additional air needs of the user.

2. An air regulator according to claim 1, wherein each of the first and second means includes a valve to permit or block flow through their respective airflow circuits, and wherein the valve of the second airflow circuit is arranged upstream of the valve of the first airflow circuit.

3. An air regulator according to claim 1, wherein said valve of the second airflow circuit comprises a valve member provided with an axial through-hole, cooperating with an air inlet conduit and communicating downstream with a feeding conduit with the valve of the first airflow circuit of the regulator, said valve member being urged with a pre-established resilient force against a valve seat of said air inlet conduit, so as to be lifted from said valve seat of the first airflow circuit when a demand for air exceeding the flow rate of said axial through-hole exists upstream of said through-hole, whereby the air conduit is placed in direct communication with the user's mouthpiece through a bypass opening.

4. An air regulator according to claim 3, wherein said valve member comprises a casing having a piston movable therein relative to the body of the casing, and means for resiliently urging the piston against the said valve seat.

5. An air regulator according to claim 3, wherein said valve member comprises a casing having an end integral therewith and resiliently movable relative to the body of the casing against the valve seat to close its opening.

* * * * *